(12) United States Patent
Song et al.

(10) Patent No.: US 9,500,646 B2
(45) Date of Patent: Nov. 22, 2016

(54) SENSOR CARTRIDGE FOR DETECTING COMPONENT OF AT LEAST ONE SAMPLE

(71) Applicant: I-SENS, INC., Seoul (KR)

(72) Inventors: Kyujeong Song, Seoul (KR); Seung Hyun Jung, Seoul (KR);
(Continued)

(*) Notice: Subject to any disclaimer, the term of this patent is extended or adjusted under 35 U.S.C. 154(b) by 0 days.

(21) Appl. No.: 14/371,339

(22) PCT Filed: Nov. 23, 2012

(86) PCT No.: PCT/KR2012/009957
§ 371 (c)(1),
(2) Date: Jul. 9, 2014

(87) PCT Pub. No.: WO2013/105731
PCT Pub. Date: Jul. 18, 2013

(65) Prior Publication Data
US 2015/0004680 A1   Jan. 1, 2015

(30) Foreign Application Priority Data
Jan. 13, 2012 (KR) .................. 10-2012-0004328

(51) Int. Cl.
*G01N 33/543* (2006.01)
*B01L 3/00* (2006.01)
(Continued)

(52) U.S. Cl.
CPC ....... *G01N 33/5438* (2013.01); *B01L 3/50273* (2013.01); *B01L 3/502715* (2013.01);
(Continued)

(58) Field of Classification Search
CPC ............ G01N 33/5438; G01N 27/327; G01N 33/48778; G01N 33/50; B01L 3/502715; B01L 3/50273
(Continued)

(56) References Cited

U.S. PATENT DOCUMENTS

| 4,246,352 A * | 1/1981 | Buddemeyer .......... C12M 41/34 |
| | | 435/287.7 |
| 2010/0143194 A1* | 6/2010 | Lee ..................... B01L 3/50273 |
| | | 422/68.1 |
| 2010/0173396 A1* | 7/2010 | Miller ................ G01N 33/5438 |
| | | 435/287.2 |

FOREIGN PATENT DOCUMENTS

| EP | 2551671 A2 | 1/2013 |
| JP | 2011-039070 A | 2/2011 |
| KR | 10-2007-0106877 A | 11/2007 |

OTHER PUBLICATIONS

International Search Report prepared by the Korean Intellectual Property Office on Mar. 26, 2013, for International Application No. PCT/KR2012/009957.

* cited by examiner

*Primary Examiner* — Jill Warden
*Assistant Examiner* — Jacqueline Brazin

(57) ABSTRACT

The present invention relates to a cartridge for sensor for detecting the concentrations of one or more components in a sample. The cartridge for sensor for detecting one or more components in a sample of the present invention not only enables quantitative measurement of one or more components in a sample by one time sample injection but also facilitates mass-production with low cost owing to the simple structure and easiness in preparation and carry. Therefore, the cartridge of the present invention can be effectively used as the biosensor cartridge for field measurement.

20 Claims, 5 Drawing Sheets

(72) Inventors: Moon Hee Choi, Seoul (KR); In Seok Jeong, Seoul (KR); Junhee Han, Seoul (KR); Geun Sig Cha, Seoul (KR)

(51) Int. Cl.
*G01N 27/327* (2006.01)
*G01N 33/487* (2006.01)
*G01N 33/50* (2006.01)
*G01N 33/94* (2006.01)

(52) U.S. Cl.
CPC ...... *G01N 27/327* (2013.01); *G01N 33/48778* (2013.01); *G01N 33/50* (2013.01); *G01N 33/946* (2013.01); *B01L 2200/0684* (2013.01); *B01L 2200/10* (2013.01); *B01L 2200/16* (2013.01); *B01L 2300/0645* (2013.01); *B01L 2300/0672* (2013.01); *B01L 2300/0816* (2013.01); *B01L 2300/0867* (2013.01); *B01L 2300/1805* (2013.01); *B01L 2400/0481* (2013.01); *B01L 2400/0683* (2013.01); *G01N 2333/4737* (2013.01)

(58) Field of Classification Search
USPC .......................................................... 422/417
See application file for complete search history.

SENSOR CARTRIDGE FOR DETECTING COMPONENT OF AT LEAST ONE SAMPLE

CROSS REFERENCE TO RELATED APPLICATIONS

This application is a national stage application under 35U.S.C. 371 and claims the benefit of PCT Application No. PCT/KR2012/009957 having an international filing date of Nov. 23, 2012, which designated the U.S., which PCT application claimed the benefit of Korean Patent Application No. 10-2012-0004328 filed Jan. 13, 2012, the disclosure of each of which is incorporated herein by reference.

TECHNICAL FIELD

The present invention relates to a cartridge for a sensor for detecting the concentrations of one or more components in a sample.

BACKGROUND ART

According to the development of modern technology in science and the accompanied increased interest in the quality of life, the importance of diagnosis/prevention of disease, food, and other environments surrounding human is growing as well. As a result, the necessity to measure the concentration of an organic material or an inorganic material in a sample is growing in order to diagnose disease or to analyze a pollutant in environment or for a specific process in the field of food chemistry and in industrial chemistry as well. Most of all, our best interest is in the biosensor which enables serial and swift analysis of multiple components and thus is regarded as one of the promising alternatives for the conventional methods in relation to clinical tests, measurement of food freshness and contamination, bioprocess control, and environment monitoring.

Biosensor is a device to measure the concentration of a target material by the following procedure: binding a biomaterial such as an enzyme, a microorganism, an antibody, a receptor and a DNA probe to an electronic or physicochemical transducer; detecting any electrochemical, optical, thermal, or piezoelectric signal generated from the reaction between the target biomaterial and the transducer; and measuring the concentration using the signals. In particular, the immunosensor using the property of forming an antigen-antibody complex is characterized by high selectivity and low detection limit because of specific recognition of antigen-antibody. Every material that can generate an antibody can be a target of such immunosensor, because of which it is highly spotlighted as a medical diagnostic sensor.

The measurement with the immunosensor is accomplished by using solid phage sandwich enzyme-linked immunosorbent assay. Solid phage sandwich enzyme-linked immunosorbent assay demonstrates excellent sensitivity, compared with any other immunoassay, owing to the specific reaction induced when an antigen binds to the fixed antibody and then label (enzyme, fluorescein, colloidal gold, latex bead) conjugated secondary antibody is bound to another immunobinding site on the antigen.

That is, in the method of solid phase competitive enzyme-linked immunosorbent assay, intervention by steric hindrance made by another material might be observed in the substrate under reaction, resulting in blocking of the signals. On the other hand, in the method of sandwich enzyme-linked immunosorbent assay, immune response is a specific reaction induced only in the immunobinding site, indicating that intervention by another material is less in the substrate, so that the signals are hardly blocked. Pathogenic bacteria, viruses and cells, the high-molecular proteins, to be analyzed in a given sample and in a standard material are conjugated with a fixed antibody, which were washed. Thereafter, a label conjugated secondary antibody is bound thereto.

Therefore, the amount of the remaining enzyme on the solid phase is in proportion to the amount of the analyte. The unbound secondary antibody label conjugates are washed away. The amount of the secondary antibody-label conjugate bound on the solid phase by immunobinding can be measured with various measurement methods according to the characteristics of different markers. Sandwich enzyme-linked immunosorbent assay demonstrating excellent specificity and sensitivity is advantageous in quantification of protein analytes. Thus, this method is generally used for the analysis of clinically important blood proteins. This method also facilitates the analysis of low-molecular analytes via competitive enzyme-linked immunosorbent assay. That is, the cartridge for sensor of the present invention is applicable to sandwich (non-competitive) enzyme-linked immunosorbent assay and competitive enzyme-linked immunosorbent assay as well.

Lab-on-a-chip is named so because it is designed to perform all the bio-experiment processes including reaction, washing, and detection in the chip with only one injection of a sample. Particularly, every necessary devices are accumulated on a few $cm^2$ sized glass, silicon, or plastic chip by using micro machining technique. That is, it is a microprocessor on which various techniques of immunology, electronic control, microfabrication, and hydrodynamics are integrated to facilitate high-speed, high-efficiency, low-cost, automatic analysis.

This technique becomes an important skill to reduce cost and time necessary for the screening of a new drug in the fast growing pharmaceutical industry. In addition, this technique is a key method that can be applied to various fields including medical diagnostic apparatus, health examination device for home or hospital, chemical or bioprocess monitoring, portable environmental pollutant analytical instrument, unmanned chemical/biological agent detection/identification apparatus for CBR, etc.

Lab-on-a chip technique is based on the capillary electrophoresis developed by Harrison et al in early 1990. They applied voltage on the both ends of a microchannel filled with a solution to cause capillary electro-osmosis forming solution flow. So, the solution flow was controlled without any additional pump or valve and separation analysis was made possible by using the capillary electrophoresis, suggesting that it was possible to build a small lab on a chip. However, even though the materials were good enough to form a microcapillary tube, it was still difficult for mass-production. Most applications of lap-on-a chip are one-time biochemical sensors, indicating that there are problems of reproducibility and production cost. To flow fluid between chambers, micro valves have to be used and washing process is required, which make the device complicated.

The present inventors tried to develop a biosensor which not only enables quantitative/qualitative measurement of one or more components in a sample by one time sample injection but also facilitates mass-production with low cost owing to the simple structure and easiness in preparation and carry. As a result, the inventors found out that one or more components could be detected by one time sample injection by using the cartridge equipped with a microfluidic channel formed between a substrate and an adhesive layer in which sample inlet-sample chamber-detecting part-disposal chamber are all connected in that order, leading to the completion of the invention.

BRIEF DESCRIPTION OF THE INVENTION

Technical Problem

It is an object of the present invention to provide a cartridge for sensor for detecting one or more components in a sample.

Technical Solution

To achieve the above object, the present invention provides a cartridge for sensor comprising a lower board, an upper board and an adhesive layer in between the two substrates to detect the concentrations of one or more components in a sample, in which sample inlet-sample chamber-detecting part-disposal chamber are connected in that order and a microfluidic channel is formed in between the boards and the adhesive layer;

the lower board is equipped with an inlet through which a sample is injected, a sample chamber to store the sample temporarily, a detecting part to detect one or more components in the sample, a disposal chamber to get rid of the sample, an air pump chamber connected to the sample chamber via air channel through which the sample temporarily stored in the sample chamber is transferred in the disposal chamber through a microfluidic channel, a pouch entry to keep reagents therein, a pouch crushing pin, a reagent pump chamber connected to the microfluidic channel by the reagent channel, and the said microfluidic channel is formed between the sample chamber and the detecting part to transfer the reagent stored in the pouch entry to the disposal chamber via the detecting part; and the upper board is equipped with a vent hole on the disposal chamber, pores on the air pump chamber and the reagent pump chamber, and a reading part introduced with a reading apparatus and stationed in the upper part of the detecting part.

At this time, when the cartridge for sensor uses electrochemical signals, the detecting part of the lower board contains an electrode part composed of one or more standard electrodes and one or more working electrodes.

In each working electrode of the electrode part, an antibody or a molecular recognition material is fixed to be reacted with different target components via immune response.

One or more label linked conjugates reacting to each target component in a sample are spreaded in one or more regions selected from the group consisting of an inlet, a sample chamber, and a microfluidic channel in between the inlet and the detecting part.

When the said cartridge for sensor uses optical signals, an antibody or a molecular recognition material capable of reacting with different target components via immune response is fixed directly on the detecting part or a detecting plate fixed with the said antibody or the molecular recognition material is introduced in the detecting part.

One or more label linked conjugates reacting to each target component in a sample are spreaded in one or more regions selected from the group consisting of an inlet, a sample chamber, and a microfluidic channel in between the inlet and the detecting part.

Advantageous Effects

As explained hereinbefore, the cartridge for a sensor for detecting one or more components in a sample of the present invention not only enables quantitative/qualitative measurement of one or more components in a sample by one time sample injection but also facilitates mass-production with low cost owing to the simple structure and easiness in preparation and carry. Therefore, the cartridge of the present invention can be effectively used as the biosensor cartridge for field measurement.

DESCRIPTION OF DRAWINGS

The application of the preferred embodiments of the present invention is best understood with reference to the accompanying drawings, wherein.

CODE EXPLANATION

Figure 1:
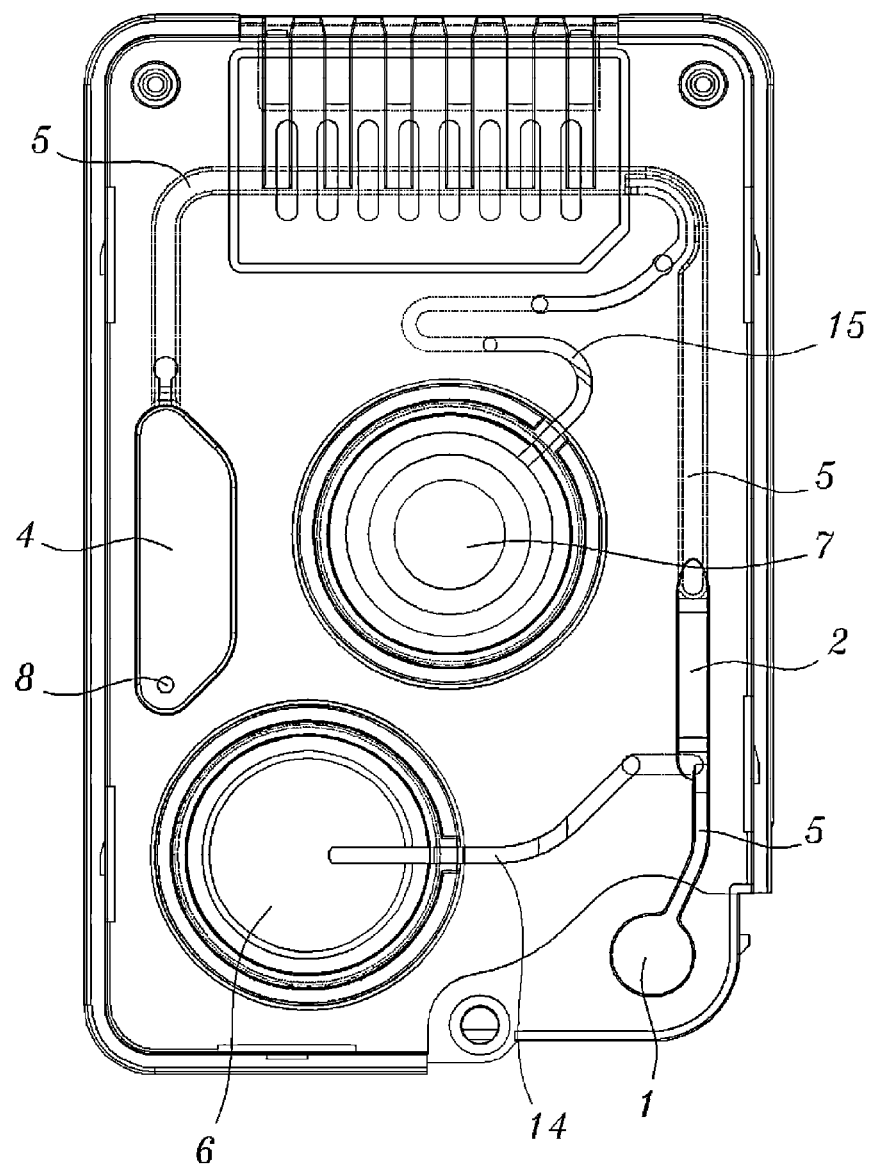
FIG. 1 is a floor map of the cartridge of the present invention according to an example of the invention.
Figure 2:
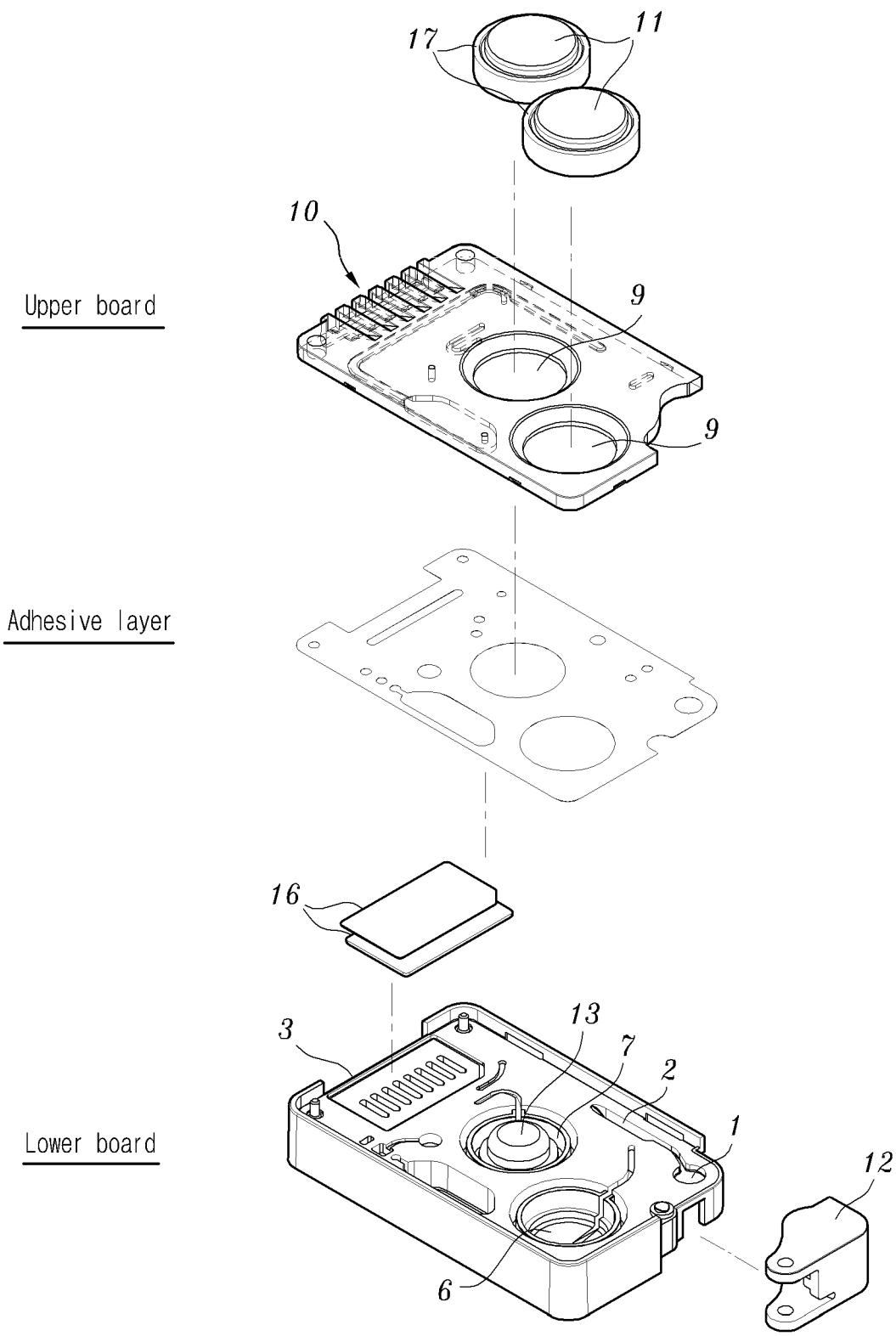
FIG. 2 is an exploded view of the cartridge of the present invention according to an example of the invention.
Figure 3:
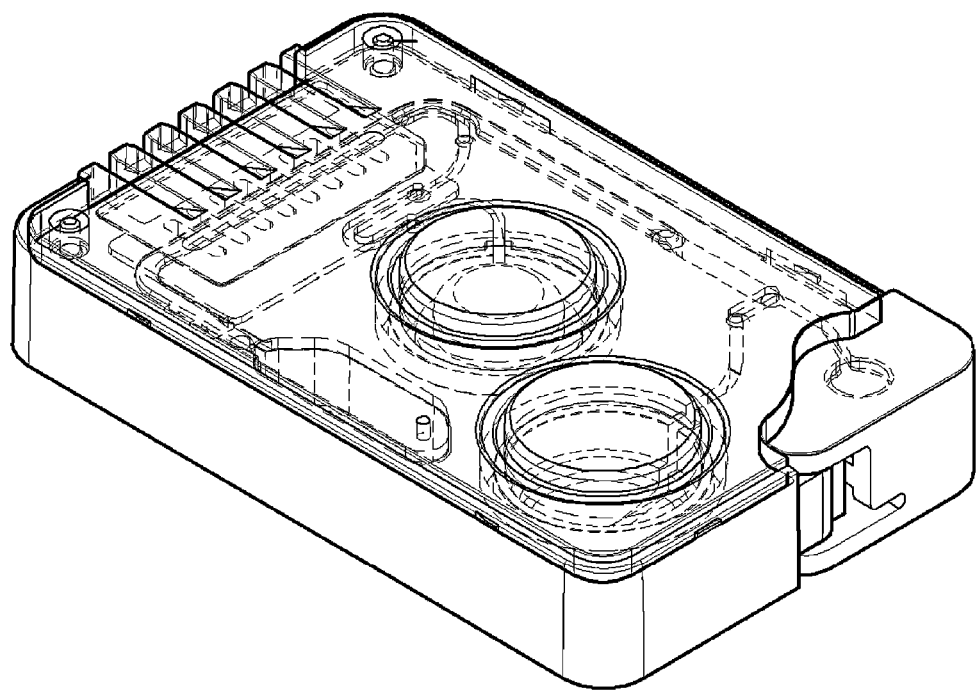
FIG. 3 is a perspective view of the cartridge of the present invention according to an example of the invention.
Figure 4:
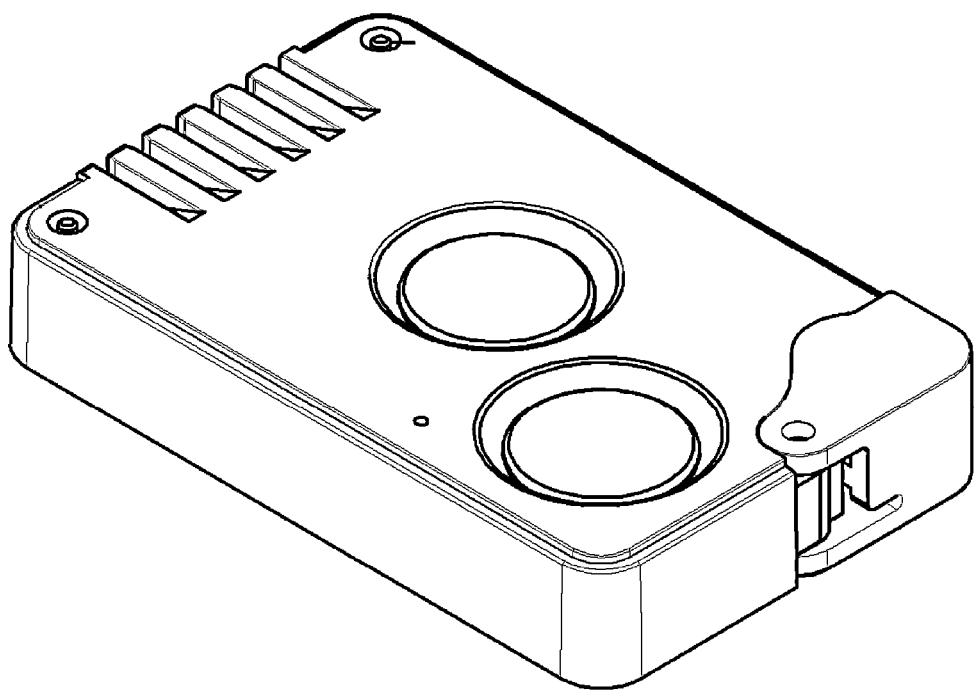
FIG. 4 is a perspective view of the cartridge of the present invention according to an example of the invention.

1: inlet
2: sample chamber
3: detecting part
4: disposal chamber
5: microfluidic channel
6: air pump chamber
7: reagent pump chamber
8: vent hole
9: pores
10: reading part
11: lid
12: inlet cover
13: pouch
14: air channel
15: reagent channel
16: electrode part or detecting plate
17: wings

BEST MODE FOR INVENTION

Hereinafter, the present invention is described in detail.

The present invention provides a cartridge for sensor for detecting one or more components in a sample, wherein the cartridge for sensor is composed of a lower board, an upper board and an adhesive layer in between the two boards;

sample inlet-sample chamber-detecting part-disposal chamber are connected in that order and a microfluidic channel is formed in between the boards and the adhesive layer;

the lower board is equipped with an inlet through which a sample is injected, a sample chamber to store the sample temporarily, a detecting part to detect one or more components in the sample, a disposal chamber to get rid of the sample, an air pump chamber connected to the sample chamber via air channel through which the sample temporarily stored in the sample chamber is transferred in the disposal chamber through a microfluidic channel, a pouch entry to keep reagents therein, a pouch crushing pin, a reagent pump chamber connected to the microfluidic channel by the reagent channel, and the said microfluidic channel is formed between the sample chamber and the detecting part to transfer the reagent stored in the pouch entry to the disposal chamber via the detecting part; and the upper board is equipped with a vent hole on the disposal chamber, pores on the air pump chamber and the reagent pump chamber, and a reading part introduced with a reading apparatus and stationed in the upper part of the detecting part.

At this time, when the cartridge for sensor uses electrochemical signals, the detecting part of the lower board contains an electrode part composed of one or more standard electrodes and one or more working electrodes.

In each working electrode of the electrode part, an antibody or a molecular recognition material is fixed to be reacted with different target components via immune response.

One or more label linked conjugates reacting to each target component in a sample are spread in one or more regions selected from the group consisting of an inlet, a sample chamber, and a microfluidic channel in between the inlet and the detecting part.

When the said cartridge for sensor uses optical signals, an antibody or a molecular recognition material capable of reacting with different target components via immune response is fixed directly on the detecting part or a detecting plate fixed with the said antibody or the molecular recognition material is introduced in the detecting part.

One or more label linked conjugates reacting to each target component in a sample are spread in one or more regions selected from the group consisting of an inlet, a sample chamber, and a microfluidic channel in between the inlet and the detecting part.

The cartridge of present invention is described in more detail by each component.

In the cartridge of the present invention, the microfluidic channel connects sample inlet-sample chamber-detecting part-disposal chamber in that order. The microfluidic channel is formed in between the substrate and the adhesive layer and plays a role as a pathway for a sample to move. Particularly, the microfluidic channel is formed between the lower board and the adhesive layer, the adhesive layer and the upper board, or the lower board and the adhesive layer, and the adhesive layer and the upper board.

When the microfluidic channel is formed between the lower board and the adhesive layer and between the upper board and the adhesive layer, pores are formed on the adhesive layer through which the microfluidic channel is connected.

In the cartridge of the present invention, the lower board is formed by the conventional plastic molding method, but not always limited thereto. Particularly, the lower board is equipped with an inlet through which a sample is injected, a sample chamber to store the sample temporarily, a detecting part to detect one or more components in the sample, a disposal chamber to get rid of the sample, an air pump chamber connected to the sample chamber via air channel through which the sample temporarily stored in the sample chamber is transferred in the disposal chamber through a microfluidic channel, a pouch entry to keep reagents therein, a pouch crushing pin, a reagent pump chamber connected to the microfluidic channel by the reagent channel, and the said microfluidic channel is formed between the sample chamber and the detecting part to transfer the reagent stored in the pouch entry to the disposal chamber via the detecting part.

In addition, a flowing backward preventing chamber can be additionally equipped in between the detecting part and the disposal chamber in order to prevent flowing backward of the sample. Precisely, one or more grooves might be equipped under the microfluidic channel connecting the electrode part and the disposal chamber or a separate flowing backward preventing chamber can be equipped.

In the cartridge of the present invention, the inlet can be prepared in the form of a round groove suitable for receiving the sample loaded by a pipette, a spoid, or a syringe, but not always limited thereto.

In the cartridge of the present invention, the sample chamber is connected to the microfluidic channel connected to the inlet. Once a sample is injected through the inlet, the sample is stored in the sample chamber by capillary phenomenon.

In the cartridge of the present invention, the detecting part is to detect one or more target components included in the sample.

Particularly, when the cartridge for sensor uses electrochemical signals, the detecting part of the lower board contains an electrode part composed of one or more standard electrodes and one or more working electrodes. In each working electrode of the electrode part, an antibody or a molecular recognition material is fixed to be reacted with different target components via immune response. One or more label linked conjugates reacting to each target component in a sample are spreaded in one or more regions selected from the group consisting of an inlet, a sample chamber, and a microfluidic channel in between the inlet and the detecting part.

The electrode part herein can additionally include a single or multiple calibration electrodes that can minimize the deviation of detection signals.

Preferably, the said calibration electrode can be composed of the first calibration electrode to detect background signals and the second calibration electrode to detect saturating signals generated from the saturated label linked conjugate.

Further, the lower board herein can additionally contain a fluidity sensing electrode to guide the substrate injection point by sensing the arrival of a sample between the detecting part and the disposal chamber.

When the said cartridge for sensor uses optical signals, an antibody or a molecular recognition material capable of reacting with different target components via immune response is fixed directly on the detecting part or a detecting plate fixed with the said antibody or the molecular recognition material is introduced in the detecting part. One or more label linked conjugates reacting to each target component in a sample are spreaded in one or more regions selected from the group consisting of an inlet, a sample chamber, and a microfluidic channel in between the inlet and the detecting part.

In the cartridge of the present invention, the said disposal chamber is to store samples and reagents finished with reaction. In general, the volume of the disposal chamber is larger than the combined volume of the sample chamber and the pouch.

In the cartridge of the present invention, the air pump chamber is connected to the sample chamber through air channel in order to send the sample temporarily stored in the sample chamber to the disposal chamber via the microfluidic channel.

At this time, the air channel connecting the air pump channel and the sample chamber is preferably positioned higher than the level of the sample stored temporarily in the sample chamber in order to prevent the flow of the sample into the air channel.

In the cartridge of the present invention, the reagent pump chamber is equipped with a pouch entry harboring reagents and a pouch crushing pin. To send reagents stored in the pouch to the disposal chamber via the detecting part, the reagent pump chamber is connected to the microfluidic channel formed in between the sample chamber and the detecting part via the reagent channel.

At this time, the reagent channel connects the reagent pump chamber and the microfluidic channel formed between the sample chamber and the detecting part, and is preferably designed to prevent the flow of a sample into the reagent channel by forcing the reagent to flow the same direction as the flow of the sample in the microfluidic channel.

In the cartridge of the present invention, the upper board can be prepared by the conventional plastic molding, but not always limited thereto.

Particularly, the upper board is equipped with a vent hole on the disposal chamber, pores on the air pump chamber and the reagent pump chamber, and a reading part introduced with a reading apparatus and stationed in the upper part of the detecting part.

In the cartridge of the present invention, the vent hole plays a role in making the sample flow smoothly through the microfluidic channel.

In the cartridge of the present invention, the pores located on the air pump chamber and the reagent pump chamber play a role in reserving the room for the pump controlling device in the reading apparatus to be functioning well.

In the cartridge of the present invention, the reading part is equipped on the upper board in the upper detecting part and plays a role in introducing the reading apparatus.

When the cartridge for sensor uses electrochemical signals, the reading apparatus equipped in the reading part is the device designed to detect electrochemical signals. When the cartridge for sensor uses optical signals, the reading apparatus equipped in the reading part is the device designed to detect optical signals.

In the cartridge of the present invention, one or more label linked conjugates reacting to each target component in a sample are spread in one or more regions selected from the group consisting of an inlet, a sample chamber, and a microfluidic channel in between the inlet and the detecting part.

When the cartridge for sensor herein uses electrochemical signals, the said label linked conjugate is a monoclonal antibody conjugate or a polyclonal antibody conjugate prepared by the reaction of an enzyme selected from the group consisting of peroxidase, alkaline phosphatase, acid phosphatase, tyrosinase and glucose oxidase with a specific antigen, suggesting that the conjugate can be selectively bound with one or more target components respectively. The conjugate herein can be an analogue conjugate that can react competitively with a target antigen, suggesting that the conjugate can react competitively with one or more target components respectively.

When the cartridge for sensor uses optical signals, the label linked conjugate is a monoclonal antibody conjugate or a polyclonal antibody conjugate prepared by the specific reaction of a fluorescein, colloidal gold, and latex bead with a target antigen. At this time, the label linked conjugate can be selectively bound with one or more target components respectively. The conjugate herein can be an analogue conjugate that can react competitively with a target antigen, suggesting that the conjugate can react competitively with one or more target components respectively.

In the cartridge of the present invention, the inlet in the lower board can have a lid on which a protrusion is formed to seal the inlet tightly. Particularly, the protrusion on the inlet lid is to seal the inlet air-tightly in order for a sample to flow smoothly when air-pump is working.

In the cartridge of the present invention, a rubber stopper is included to seal the air pump chamber and the reagent pump chamber equipped in the lower board to help the air pump be functioning well. Particularly, the rubber stopper is equipped with wings to seal the air pump chamber and the reagent pump chamber completely. At this time, the wing covers the lower board or the adhesive layer and is fixed by the upper board, but not always limited thereto.

In the cartridge of the present invention, the separation of the air pump and the reagent pump is to prevent the backward flow of a sample by maintaining pressure by pushing the air pump completely down until the reaction in the detecting part is finished.

When a sample flows backward, false signals made not by immune response but by the label linked conjugate remaining after the immune response and thus flowing back into the electrode part, which would be a problem. Therefore, the air pump not only plays an important role in transferring a sample but also plays a role in preventing backward flowing to increase detection accuracy.

In addition, in the cartridge of the present invention, a pouch is included in the pouch entry in the reagent pump chamber to provide the stored reagent when it is broken by the crushing pin during the pumping of the reagent pump.

When the cartridge for sensor uses electrochemical signals, the reagent stored in the said pouch can be any single substrate selected from the group consisting of naphthol AS, naphthol AS-BI, naphthol AS-D, naphthol AS-MX, p-aminophenylphosphate, hydrogen peroxide, and glucose, or any combination of those. The substrate, at this time, plays a role in generating electrochemical signals by inducing enzyme-substrate reaction with the enzyme of the label linked conjugate.

When the cartridge for sensor uses optical signals, the washing buffer for the reagent stored in the pouch can be the buffer generally used for immune response. The washing buffer at this time is to wash off the remaining materials not reacted with the antibody fixed on the detecting part, which is helpful for more accurate detection.

In the cartridge of the present invention, a hotplate entry is additionally installed to regulate reaction temperature in the lower side of the lower board where the detecting part is located. At this time, a single or multiple vent holes can be additionally equipped on the side of the lower board where the detecting part is located in order to increase heat transfer efficiency.

The enzyme-substrate reaction is affected by temperature, suggesting that the signals can be different by the temperature of the surrounding area during the detection. To prevent detecting false signal, a hotplate is introduced over the electrode part or the entire lower board to maintain temperature regularly, which plays an important role in reducing deviations made by false signals generated by different temperature of the surrounding area. It is another role of the hotplate added herein to maintain temperature suitable for the optimum enzyme activity, so as to provide the effect of amplification of signals and to increase immune response between antigen-antibody.

The sample herein can be blood, tears, sweat, saliva, or urine of mammals, or any solution or fluid generated from food or environment.

Particularly, a target component is exemplified by abnormal proteins released in body fluid such as C-reactive protein, troponin I troponin T, myoglobin, CK-MB, B-type natriuretic peptide, alpha-fetoprotein and carcino-embryonic antigen; cholesterol; hormone such as human chorionic gonadotropin (HCG); viruses such as HBV, HCV, HIV, and influenza; pathogenic bacteria such as *H. Pylori*; misused or overused drugs such as steroid; narcotics; antibiotics included in agricultural/livestock products; allergens in food; and proteins or bacteria causing food poisoning, but not always limited thereto.

When the cartridge for sensor of the present invention uses electrochemical signals, the cartridge can be run by the sandwich enzyme-linked immunosorbent assay comprising the following steps:

inserting a sample to the inlet and storing the sample temporarily in the sample chamber (step 1);

forming a target component-label linked conjugate by the reaction between a target component in the sample and a label linked conjugate spread in one or more regions of the cartridge selected from the group consisting of the inlet, the sample chamber, and the microfluidic channel formed between the inlet and the detecting part (step 2);

forming an antibody-target component-label linked conjugate by inducing immune response between the target component-label linked conjugate formed in step 2 and the antibody fixed on the electrode part in the course of transferring the sample stored temporarily in the sample chamber to the disposal chamber by activating the air pump (step 3); and generating electrochemical signals by reacting the antibody-target component-label linked conjugate formed on the electrode part in step 3 with the substrate included in the reagent in the course of transferring the sample to the disposal chamber by activating the reagent pump to break the pouch in the reagent pump chamber (step 4).

At this time, the electrochemical signal generated in step 4 is transmitted to the reading apparatus via the reading part equipped in the upper board to detect the target component quantitatively and qualitatively.

In the meantime, the sample can be forced to make a round trip a few times in the detecting part by regulating the air pump in step 3 before the sample is transferred into the disposal chamber. This step can be additionally included to increase the chance of immune response between the target component-label linked conjugate and the antibody fixed on the working electrode. Herein, any molecular recognition material used in the field of biosensor technology can be used without limitation instead of the antibody fixed on the working electrode.

In step 2, the target component-label linked conjugate can be formed before or after the activation of the air pump of step 3 according to where the label linked conjugate is located in the cartridge.

When the cartridge for sensor of the present invention uses electrochemical signals, the cartridge can be run by the competitive enzyme-linked immunosorbent assay comprising the following steps:

inserting a sample to the inlet and storing the sample temporarily in the sample chamber (step 1);

forming a target component-antibody label linked conjugate by combining a target component in the sample and an antibody label linked conjugate spreaded in one or more regions selected from the group consisting of the inlet, the sample chamber, and the microfluidic channel formed between the inlet and the detecting part, or distributing a target component in the sample and an analogue marker conjugate respectively and competitively (step 2);

forming an analogue-antibody label linked conjugate by combining the analogue fixed on the working electrode and the antibody label linked conjugate that does not form a target component-antibody label linked conjugate because of competition of the target component-antibody label linked conjugate formed in step 2 and the analogue fixed on the working electrode, or forming an antibody-analogue label linked conjugate and an antibody-target component conjugate by competitive reaction of the target component and the analogue label linked conjugate distributed together with the antibody fixed on the working electrode (step 3): and generating electrochemical signals by reacting the enzyme in the analogue-antibody label linked conjugate or the antibody-analogue label linked conjugate formed on the working electrode in step 3 with the substrate included in the reagent during transferring the sample to the disposal chamber by activating the reagent pump to break the pouch in the reagent pump chamber (step 4).

At this time, the electrochemical signal generated in step 4 is transmitted to the reading apparatus via the reading part equipped on the upper board, leading to the quantitative/qualitative detection of the target component. Unlike sandwich enzyme-linked immunosorbent assay, this method is to detect the target component quantitatively and qualitatively by measuring the decrease of signal over the concentration of the target component.

In the meantime, the sample can be forced to make a round trip several times in the detecting part by regulating the air pump in step 3 before the sample is transferred into the disposal chamber. This process is to increase immune response between each label linked conjugate and the antibody or the molecular recognition material fixed on the working electrode, and can be additionally included. Herein, any molecular recognition material used in the field of biosensor technology can be used without limitation instead of the antibody fixed on the working electrode.

Each reaction of the label linked conjugate with the target component in step 2 is performed to form a target component-antibody label linked conjugate before or after activating the air pump of step 3 according to the location of the label linked conjugate in the cartridge or another reaction between the target component and the analogue label linked conjugate can be competitively induced.

In addition, when the cartridge for sensor of the present invention uses optical signals, the cartridge can be run by the sandwich enzyme-linked immunosorbent assay comprising the following steps:

inserting a sample to the inlet and storing the sample temporarily in the sample chamber (step 1);

forming a target component-label linked conjugate by combining a target component in the sample and a label linked conjugate spreaded in one or more regions selected from the group consisting of the inlet, the sample chamber, and the microfluidic channel formed between the inlet and the detecting part (step 2);

forming an antibody-target component-label linked conjugate by inducing immune response between the target component-label linked conjugate formed in step 2 and the antibody fixed on the detecting part or detecting plate in the course of transferring the sample stored temporarily in the sample chamber to the disposal chamber by activating the air pump (step 3);

washing the remaining substances which failed to form an antibody-target component-label linked conjugate with the antibody fixed on the detecting part or detecting plate in step 3, in the course of transferring the reagent to the disposal chamber by activating the reagent pump to break the pouch in the reagent pump chamber (step 4); and irradiating excitation light for the measurement of fluorescence spectrum or light for spectrometry (step 5).

At this time, the optical signal generated in step 5 is transmitted to the reading apparatus via the reading part for the quantitative/qualitative measurement of the target component.

In the meantime, the sample can be forced to make a round trip several times in the detecting part by regulating the air pump in step 3 before the sample is transferred into the disposal chamber. This process is to increase immune response between each target component-label linked conjugate and the antibody or the molecular recognition material fixed on the detecting part or detecting plate, and can be additionally included. Herein, any molecular recognition material used in the field of biosensor technology can be used without limitation instead of the antibody fixed on the detecting part or detecting plate.

In step 2, the target component-label linked conjugate can be formed before or after the activation of the air pump of step 3 according to where the label linked conjugate is located in the cartridge.

When the cartridge for sensor of the present invention uses optical signals, the cartridge can be run by the competitive enzyme-linked immunosorbent assay comprising the following steps:

inserting a sample to the inlet and storing the sample temporarily in the sample chamber (step 1);

forming a target component-antibody label linked conjugate by combining a target component in the sample and an antibody label linked conjugate spreaded in one or more regions selected from the group consisting of the inlet, the sample chamber, and the microfluidic channel formed between the inlet and the detecting part, or distributing a target component in the sample and an analogue label linked conjugate respectively and competitively (step 2);

forming an analogue-antibody label linked conjugate by combining the analogue fixed on the working electrode and the antibody label linked conjugate that does not form a target component-antibody label linked conjugate because of competition of the target component-antibody label linked conjugate formed in step 2 and the analogue fixed on the working electrode, or forming an antibody-analogue label linked conjugate and an antibody-target component conjugate by competitively reacting the target component and the analogue label linked conjugate distributed together with the antibody fixed on the working electrode (step 3);

washing the remaining substances which failed to form an antibody-analogue label linked conjugate or an analogue-antibody label linked conjugate with the antibody fixed on the detecting part in step 3, in the course of transferring the reagent to the disposal chamber by activating the reagent pump to break the pouch in the reagent pump chamber (step 4); and irradiating excitation light for the measurement of fluorescence spectrum or light for spectrometry (step 5).

At this time, the optical signal generated in step 5 is transmitted to the reading apparatus via the reading part for the quantitative/qualitative measurement of the target component. Unlike sandwich enzyme-linked immunosorbent assay, this method is to detect the target component quantitatively and qualitatively by measuring the decrease of signal over the concentration of the target component.

In the meantime, the sample can be forced to make a round trip several times in the detecting part by regulating the air pump in step 3 before the sample is transferred into the disposal chamber. This process is to increase immune response between each label linked conjugate and the antibody or the molecular recognition material fixed on the detecting part or detecting plate, and can be additionally included. Herein, any molecular recognition material used in the field of biosensor technology can be used without limitation instead of the antibody fixed on the detecting part or detecting plate.

In step 2, the target component-label linked conjugate can be formed before or after the activation of the air pump of step 3 according to where the label linked conjugate is located in the cartridge, or the target component might compete with the analogue label linked conjugate to be distributed.

As explained hereinbefore, the cartridge for sensor for detecting one or more components in a sample of the present invention not only enables quantitative/qualitative measurement of one or more components in a sample by one time sample injection but also facilitates mass-production with low cost owing to the simple structure and easiness in preparation and carry. Therefore, the cartridge of the present invention can be effectively used as the biosensor cartridge for field measurement.

Mode for Invention

Practical and presently preferred embodiments of the present invention are illustrative as shown in the following Examples, Experimental Examples and Manufacturing Examples. However, it will be appreciated that those skilled in the art, on consideration of this disclosure, may make modifications and improvements within the spirit and scope of the present invention.

EXAMPLE 1

Preparation of Cartridge for Measuring C-Reactive Protein (1) Preparation of Electrode Part Carbon paste was screen-printed on polyethylene terephthalate (PET) film by using patterned stencil (thickness: 7-15 μm). The carbon paste printed film board was dried at 130° C. for 10 minutes, and then heat was eliminated at room temperature for 10 minutes. Ag/AgCl paste was screen-printed on the above carbon paste printed board by using stencil by the same manner as the above. The printed film board was dried at 130° C. for 10 minutes and then heat was eliminated at room temperature. Laser-cutting was performed to cut the board into a right size for the electrode part of the cartridge.

(2) Preparation of Lower Board, Upper Board, Inlet Lid, and Adhesive Layer

The lower board, upper board, and inlet lid were constructed based on mold design which made the assembly of those perfectly tight without any spare room between the channel and other parts. According to the kinds of plastic material, the lower board, upper board, and inlet lid were prepared by injection molding. The adhesive layer adheres the upper board and the lower board together using double-sided tape (customized to fit the requirement), leaving pores which are the channels to connect the upper board and the lower board.

(3) Antibody Fixation on Working Electrode

Streptavidin was added to PBS containing a stabilizer at the concentration of 50 μg/ml. This solution was loaded on the working electrode (2 μl/time). The electrode was dried at 25° C. with 40% humidity, which was passed through a washer with a washing buffer (PBS spray and air spray). After washing the electrode, the remaining washing buffer was eliminated, followed by drying at 25° C. with 40% humidity for an hour. Biotin conjugated antibody solution (PBS containing a stabilizer) was prepared at the concentration of 0.1 mg/ml, which was loaded on the working electrode 2 μl at a time, followed by drying at 25° C. with 40% humidity for 1 hour, resulting in the preparation of the electrode to be equipped in the cartridge.

(4) Spreading Label Linked Conjugate on Sample Chamber

The label linked conjugate was spread on the sample chamber to form a complex with the antigen, the target material for detection, coming in through the sample inlet. For the antigen-antibody reaction, the label linked conjugate needs to be evenly spread on the sample chamber. To maintain the enzyme activity for a long time, the label linked conjugate solution preferably comprises the composition determined by a required experiment. The general solution is usually coagulated in the spot where it is loaded on the plastic cartridge, suggesting that the solution does not flow the surface. So, PBS containing 0.5% Tween 20 was primarily spread on the sample chamber. Then, 10 μl of the solution supplemented with the label linked conjugate and a stabilizer was distributed in the sample chamber, followed by freeze-drying at −40° C.

(5) Preparation of Pouch Containing Reagent

Plastic reagent pouches in installable size for the reagent pump chamber (cylindrical container, diameter: 7.2 mm, depth: 4.0 mm) were prepared in large quantities as small plastic containers by forming vacuum. 150 μl of the substrate solution was loaded in the container. The plastic reagent pouch was covered tightly with an aluminum cover and the aluminum cover and the reagent pouch wing were glued together by using a heat sealing apparatus to seal completely. The prepared reagent pouches were cut by the inner diameter of the reagent pump chamber so as to be installed in the reagent pump chamber without any spare room, resulting in single reagent pouches.

(6) Preparation of Rubber Stopper Acting as Pump

The air pump chamber and the reagent pump chamber were located on the lower board in equal sizes and shapes, which had rubber stoppers. At this time, the rubber stopper had to be contacted with the whole surface area of each chamber and had double wings to increase air-tight property with the dome shaped upper side. The rubber stopper was prepared by pouring a rubber solution in the mold designed as described above via injection molding.

(7) Assembly of Each Part

Each part prepared in the above (1)~(6) were assembled as follows to prepare the cartridge.

First, the electrode part was placed in the detecting part on the lower board. The reagent pouch was placed in the reagent pump chamber, on which the adhesive layer was layered. The rubber stoppers were pushed in the air pump chamber and the reagent pump chamber. Then, the upper board was contacted thereto, leading to the assembly of the cartridge. The inlet lid was pushed in the inlet lid detachment part installed in the lower board to complete the cartridge.

EXAMPLE 2

Preparation of Cartridge for Measuring AMP (Amphetamine), COC (Cocaine), OPI (Morphine among Opiates), BZD (Benzodiazepine), and MET (Methamphetamine)

(1) Preparation of Electrode Part

Carbon paste was screen-printed on polyethylene terephthalate (PET) film by using patterned stencil (thickness: 7-15 μm). The carbon paste printed film board was dried at 130° C. for 10 minutes, and then heat was eliminated at room temperature for 10 minutes. Ag/AgCl paste was screen-printed on the above carbon paste printed board by using stencil by the same manner as the above. The printed film board was dried at 130° C. for 10 minutes and then heat was eliminated at room temperature. Laser-cutting was performed to cut the board into a right size for the electrode part of the cartridge.

(2) Preparation of Lower Board, Upper Board, Inlet Lid, and Adhesive Layer

The lower board, upper board, and inlet lid were constructed based on mold design which made the assembly of those perfectly tight without any spare room between the channel and other parts. According to the kinds of plastic material, the lower board, upper board, and inlet lid were prepared by injection molding. The adhesive layer adheres the upper board and the lower board together using double-sided tape (customized to fit the requirement), leaving pores which are the channels to connect the upper board and the lower board.

(3) Fixation of Competitive Antibody Conjugate on Working Electrode

When the detection target (antigen) had a small molecular weight, a protein (generally BSA or BTG) was conjugated to the small molecular weight antigen regardless of immune response in order to aid antigen-antibody complex formation. The antigen conjugate was loaded in PBS containing a stabilizer at the concentration of 20 μg/ml, which was loaded on the working electrode 2 μl at a time. The electrode was dried at 25° C. with 40% humidity, which was passed through a washer with PBS (PBS spray and air spray) to wash the electrode. Then, the remaining washing buffer was eliminated. The electrode was dried again at 25° C. with 40% humidity for a hour, which was installed in the cartridge. The detection target is investigated by measuring the signal reduction caused by the antibody conjugate by competitive immune response between the target material (antigen) and the antigen conjugate fixed on the working electrode.

(4) Spreading Label Linked Conjugate on Sample Chamber

The label linked conjugate was spreaded on the sample chamber to form a complex with the antigen, the target material for detection, coming in through the sample inlet. For the antigen-antibody reaction, the label linked conjugate needs to be evenly spreaded on the sample chamber. To maintain the enzyme activity for a long time, the label linked conjugate solution preferably contains a stabilizer. The general solution is usually coagulated in the spot where it is loaded on the plastic cartridge, suggesting that the solution does not flow the surface. So, PBS containing 0.5% Tween 20 was primarily spreaded on the sample chamber. Then, 10 μl of the solution supplemented with the label linked conjugate and a stabilizer was distributed in the sample chamber, followed by freeze-drying.

(5) Preparation of Pouch Containing Reagent

Plastic reagent pouches in installable size for the reagent pump chamber (cylindrical container, diameter: 7.2 mm, depth: 4.0 mm) were prepared in large quantities as small plastic containers by forming vacuum. 150 μl of the substrate solution was loaded in the container. The plastic reagent pouch was covered tightly with an aluminum cover and the aluminum cover and the reagent pouch wing were glued together by using a heat sealing apparatus to seal completely. The prepared reagent pouches were cut by the inner diameter of the reagent pump chamber so as to be installed in the reagent pump chamber without any spare room, resulting in single reagent pouches.

(6) Preparation of Rubber Stopper Acting as Pump

The air pump chamber and the reagent pump chamber were located on the lower board in equal sizes and shapes, which had rubber stoppers. At this time, the rubber stopper had to be contacted with the whole surface area of each chamber and had double wings to increase air-tight property with the dome shaped upper side. The rubber stopper was prepared by pouring a rubber solution in the mold designed as described above via injection molding.

(7) Assembly of Each Part

Each part prepared in the above (1)~(6) were assembled as follows to prepare the cartridge.

First, the electrode part was placed in the detecting part on the lower board. The reagent pouch was placed in the reagent pump chamber, on which the adhesive layer was layered. The rubber stoppers were pushed in the air pump chamber and the reagent pump chamber. Then, the upper board was contacted thereto, leading to the assembly of the cartridge. The inlet lid was pushed in the inlet lid detachment part installed in the lower board to complete the cartridge.

EXAMPLE 3

Preparation of Cartridge for Measuring C-Reactive Protein Using Fluorescein Conjugate (1) Preparation of Antibody Fixed Board The antibody against the detection target antigen was sprayed on the polystyrene film by using a dispenser (25 μg/ml), particularly in the region of the detecting part that would be exposed on the upper board. The film was dried at 25° C. with 40% humidity for 30 minutes, followed by distribution of a blocking solution. The film was dried again at 25° C. with 40% humidity for 1 hour, followed by laser cutting into the installable size for the electrode part of the cartridge.

(2) Preparation of Lower Board, Upper Board, Inlet Lid, and Adhesive Layer

The lower board, upper board, and inlet lid were constructed based on mold design which made the assembly of those perfectly tight without any spare room between the channel and other parts. According to the kinds of plastic material, the lower board, upper board, and inlet lid were prepared by injection molding. In the meantime, the adhesive layer was prepared to adhere the lower board and the upper board together by using double-sided tape (customized to fit the requirement).

(3) Spreading Fluorescein Conjugate on Sample Chamber

The fluorescein conjugate was spreaded on the sample chamber to form a complex with the antigen, the target material for detection, coming in through the sample inlet. For the antigen-antibody reaction, the fluorescein conjugate needs to be evenly spreaded on the sample chamber. To maintain the enzyme activity for a long time, the fluorescein conjugate solution preferably comprises the composition determined by a required experiment. The general solution is usually coagulated in the spot where it is loaded on the plastic cartridge, suggesting that the solution does not flow the surface. So, PBS containing 0.5% Tween 20 was primarily spreaded on the sample chamber. Then, 30 μl of the solution supplemented with the fluorescein conjugate and a stabilizer was distributed in the sample chamber, followed by freeze-drying.

(4) Preparation of Pouch Containing Washing Buffer

Plastic reagent pouches in installable size for the reagent pump chamber (cylindrical container, diameter: 7.2 mm, depth: 4.0 mm) were prepared in large quantities as small plastic containers by forming vacuum. 150 μl of the washing buffer was loaded in the container. The plastic reagent pouch was covered tightly with an aluminum cover and the aluminum cover and the reagent pouch wing were glued together by using a heat sealing apparatus to seal completely. The prepared reagent pouches were cut by the inner diameter of the reagent pump chamber so as to be installed in the reagent pump chamber without any spare room, resulting in single reagent pouches.

(5) Preparation of Rubber Stopper Acting as Pump

The air pump chamber and the reagent pump chamber were located on the lower board in equal sizes and shapes, which had rubber stoppers. At this time, the rubber stopper had to be contacted with the whole surface area of each chamber and had double wings to increase air-tight property with the dome shaped upper side. The rubber stopper was prepared by pouring a rubber solution in the mold designed as described above via injection molding.

(6) Assembly of Each Part

Each part prepared in the above (1)~(5) were assembled as follows to prepare the cartridge.

First, the electrode part was placed in the detecting part on the lower board. The reagent pouch was placed in the reagent pump chamber, on which the adhesive layer was layered. The rubber stoppers were pushed in the air pump chamber and the reagent pump chamber. Then, the upper board was contacted thereto, leading to the assembly of the cartridge. The inlet lid was pushed in the inlet lid detachment part installed in the lower board to complete the cartridge.

EXAMPLE 4

Preparation of Cartridge for Measuring C-Reactive Protein Gold Using Colloidal Gold and Latex Bead (1) Preparation of Antibody Fixed Board The antibody against the detection target antigen was sprayed on the polystyrene film by using a dispenser (25 μg/ml), particularly in the region of the detecting part that would be exposed on the upper board. The film was dried at 25° C. with 40% humidity for 30 minutes, followed by distribution of a blocking solution. The film was dried again at 25° C. with 40% humidity for 1 hour, followed by laser cutting into the installable size for the electrode part of the cartridge.

(2) Preparation of Lower Board, Upper Board, Inlet Lid, and Adhesive Layer

The lower board, upper board, and inlet lid were constructed based on mold design which made the assembly of those perfectly tight without any spare room between the channel and other parts. According to the kinds of plastic material, the lower board, upper board, and inlet lid were prepared by injection molding. In the meantime, the adhesive layer was prepared to adhere the lower board and the upper board together by using double-sided tape (customized to fit the requirement).

(3) Spreading Colloidal Gold and Latex Bead Conjugate on Sample Chamber

The colloidal gold and latex bead conjugate was spreaded on the sample chamber to form a complex with the antigen, the target material for detection, coming in through the sample inlet. For the antigen-antibody reaction, the colloidal gold and latex bead conjugate needs to be evenly spreaded on the sample chamber. To increase stability of the colloidal gold and latex bead, the colloidal gold and latex bead conjugate solution preferably comprises the composition determined by a required experiment. The general solution is usually coagulated in the spot where it is loaded on the plastic cartridge, suggesting that the solution does not flow the surface. So, PBS containing 0.5% Tween 20 was primarily spreaded on the sample chamber. Then, 30 µl of the solution supplemented with the colloidal gold and latex bead conjugate and a stabilizer was distributed in the sample chamber, followed by freeze-drying.

(4) Preparation of Pouch Containing Washing Buffer

Plastic reagent pouches in installable size for the reagent pump chamber (cylindrical container, diameter: 7.2 mm, depth: 4.0 mm) were prepared in large quantities as small plastic containers by forming vacuum. 150 µl of the washing buffer was loaded in the container. The plastic reagent pouch was covered tightly with an aluminum cover and the aluminum cover and the reagent pouch wing were glued together by using a heat sealing apparatus to seal completely. The prepared reagent pouches were cut by the inner diameter of the reagent pump chamber so as to be installed in the reagent pump chamber without any spare room, resulting in single reagent pouches.

(5) Preparation of Rubber Stopper Acting as Pump

The air pump chamber and the reagent pump chamber were located on the lower board in equal sizes and shapes, which had rubber stoppers. At this time, the rubber stopper had to be contacted with the whole surface area of each chamber and had double wings to increase air-tight property with the dome shaped upper side. The rubber stopper was prepared by pouring a rubber solution in the mold designed as described above via injection molding.

(6) Assembly of Each Part

Each part prepared in the above (1)~(5) were assembled as follows to prepare the cartridge.

First, the electrode part was placed in the detecting part on the lower board. The reagent pouch was placed in the reagent pump chamber, on which the adhesive layer was layered. The rubber stoppers were pushed in the air pump chamber and the reagent pump chamber. Then, the upper board was contacted thereto, leading to the assembly of the cartridge. The inlet lid was pushed in the inlet lid detachment part installed in the lower board to complete the cartridge.

EXPERIMENTAL EXAMPLE 1

C-Reactive Protein (CRP)-Sandwich Analysis of Single Detection Material

The concentration of C-reactive protein was measured by sandwich enzyme-linked immunosorbent assay with the cartridge prepared in Example 1.

Precisely, serum confirmed not to contain CRP (CRP free serum, Cat. #8CFS, Hytest) was purchased. CRP (CRP antigen, Prod. Code 3375-1300, Bioprocessing) was added at the wanted concentration to the serum. The prepared sample proceeded to measurement of CRP concentration with the analyzer (ADVIA 2400, Siemens) provided by GCLabs. The cartridge for measuring C-reactive protein prepared in Example 1 was installed in the reading apparatus prepared herein, to which the prepared sample was loaded. After required reading process, current was measured by using a designated device (1030B, CHInstruments) and the results are shown in the below Table 1.

TABLE 1

| | CRP | | | | | | | | |
|---|---|---|---|---|---|---|---|---|---|
| | 20 mg/L | 10 mg/L | 8 mg/L | 5 mg/L | 3 mg/L | 1 mg/L | 0.3 mg/L | 0.1 mg/L | 0 mg/L |
| Current, µA | 16.51 | 12.26 | 12.50 | 10.37 | 7.91 | 4.36 | 3.22 | 2.82 | 2.20 |
| | 16.53 | 12.55 | 12.35 | 10.49 | 7.88 | 4.36 | 3.01 | 2.63 | 2.13 |
| | 16.77 | 13.00 | 12.51 | 10.85 | 7.25 | 4.15 | 3.13 | 2.58 | 2.09 |
| | 16.79 | 13.78 | 12.66 | 10.28 | 7.19 | 4.07 | 3.17 | 2.66 | 2.22 |
| Mean | 16.65 | 12.90 | 12.51 | 10.50 | 7.56 | 4.24 | 3.13 | 2.67 | 2.16 |
| deviation, | 0.15 | 0.66 | 0.13 | 0.25 | 0.39 | 0.15 | 0.09 | 0.10 | 0.06 |
| CV (%) | 0.90 | 5.14 | 1.01 | 2.38 | 5.17 | 3.49 | 2.86 | 3.88 | 2.80 |

As shown in Table 1, the sample was loaded in the cartridge for measuring C-reactive protein to obtain current values over the CRP concentration. CRP concentration was calculated based on the current values. The measuring range includes the clinically meaningful range for diagnose (0.1 mg/L or under: cardiovascular disease low risk group, 0.1-0.3 mg/L: cardiovascular disease average risk group, 0.3 mg/L or up: cardiovascular disease high risk group). It was also measured in the range of CV % that has been generally accepted with the measurement using other CRP detection devices (<13%).

EXPERIMENTAL EXAMPLE 2

Competitive Analysis of 5 target materials; AMP (Amphetamine), COC (Cocaine), OPI (Morphine Among Opiates), BZD (Benzodiazepine), and MET (Methamphetamine)

The concentrations of AMP (Amphetamine), COC (Cocaine), OPI (Morphine among Opiates), BZD (Benzodiazepine), and MET (Methamphetamine) were simultaneously analyzed by using the cartridge prepared in Example 2.

Particularly, samples were prepared by adding psychotropic drugs and narcotics (S(+)-Amphetamine, Cat.#A-008; Benzoylecgonine(COC), Cat.#B-004; Morphine, Cat.#M-005; Oxazepam(BZD), Cat.#O-902; (±)-Methamphetamine, Cat.#M-009, Cerilliant) to saliva (Pooled Human Saliva, Cat.#NC0003593, Fisher Scientific) at different concentrations. Psychotropic drugs and narcotics could only be handled by those who had permission, so other organizations or other analysis equipments were not allowed to be used. The cartridge for detecting 5 psychotropic drugs and narcotics of the invention was installed in the reading apparatus prepared in this invention, to which the prepared sample was loaded. After required reading process, current was measured by using a designated device (1030B, CHInstruments) and the results are shown in the below Tables 2-6.

TABLE 2

| AMP | 75 µg/L | 50 µg/L | 25 µg/L | 0 µg/L |
|---|---|---|---|---|
| Current, | 0.95 | 1.12 | 1.40 | 2.45 |
| µA | 0.96 | 1.21 | 1.39 | 2.41 |
|  | 0.99 | 1.14 | 1.51 | 2.23 |
|  | 0.89 | 1.10 | 1.43 | 2.11 |
| Mean | 0.95 | 1.14 | 1.43 | 2.30 |
| deviation, | 0.04 | 0.05 | 0.05 | 0.16 |
| CV (%) | 4.57 | 4.22 | 3.80 | 6.94 |

TABLE 3

| COC | 30 µg/L | 20 µg/L | 10 µg/L | 0 µg/L |
|---|---|---|---|---|
| Current, | 0.86 | 1.10 | 1.39 | 2.31 |
| µA | 0.75 | 1.12 | 1.41 | 2.12 |
|  | 0.79 | 1.05 | 1.45 | 2.00 |
|  | 0.81 | 1.15 | 1.44 | 2.09 |
| Mean | 0.80 | 1.11 | 1.42 | 2.13 |
| deviation, | 0.04 | 0.04 | 0.03 | 0.13 |
| CV (%) | 5.62 | 3.90 | 1.97 | 6.10 |

TABLE 4

| OPI | 60 µg/L | 40 µg/L | 20 µg/L | 0 µg/L |
|---|---|---|---|---|
| Current, | 1.04 | 1.21 | 1.59 | 2.12 |
| µA | 0.96 | 1.19 | 1.55 | 2.04 |
|  | 1.08 | 1.17 | 1.61 | 2.13 |
|  | 1.01 | 1.20 | 1.62 | 2.24 |
| Mean | 1.02 | 1.19 | 1.59 | 2.13 |
| deviation, | 0.05 | 0.02 | 0.03 | 0.08 |
| CV (%) | 4.98 | 1.52 | 2.07 | 3.92 |

TABLE 5

| BZD | 75 µg/L | 50 µg/L | 25 µg/L | 0 µg/L |
|---|---|---|---|---|
| Current, | 0.95 | 1.19 | 1.36 | 2.34 |
| µA | 0.89 | 1.21 | 1.39 | 2.02 |
|  | 0.87 | 1.14 | 1.45 | 2.25 |
|  | 0.89 | 1.13 | 1.52 | 2.09 |
| Mean | 0.90 | 1.17 | 1.43 | 2.18 |
| deviation, | 0.03 | 0.04 | 0.07 | 0.15 |
| CV (%) | 3.89 | 3.31 | 4.94 | 6.72 |

TABLE 6

| MET | µg/L | µg/L | µg/L | µg/L |
|---|---|---|---|---|
| Current, | 0.78 | 1.01 | 1.52 | 2.03 |
| µA | 0.87 | 1.14 | 1.47 | 2.31 |
|  | 0.85 | 1.18 | 1.51 | 2.22 |
|  | 0.89 | 1.08 | 1.63 | 2.24 |
| Mean | 0.85 | 1.10 | 1.53 | 2.20 |
| deviation, | 0.05 | 0.07 | 0.07 | 0.12 |
| CV (%) | 5.55 | 6.72 | 4.47 | 5.44 |

As shown in Tables 2~6, based on the concentration of each psychotropic substance and narcotic determined and allowed by Substance Abuse and Mental Health Services Administration, US Department of Health and Human Service, the concentration of each target sample was evaluated. Current whose signal changes could be recognized was obtained in the range of around 50% by the standard concentration mentioned above. Therefore, it was confirmed that mis/over-use of the 5 psychotropic substances/narcotics could be determined by using the cartridge prepared in Example 2.

EXPERIMENTAL EXAMPLE 3

Evaluation of Detection Strength Over the Numbers of Round Trip Made by the Sample in the Detecting Part The sample was made to have round trip several times in the detecting part by regulating the air pump, which was to increase the chances of immune response between the target component-label linked conjugate and the antibody fixed on the working electrode, the detecting part, or the detecting plate, followed by measuring the changes of detection strength.

Particularly, the method for detecting electrochemical signals was used. The sample was made to have round trip 0~50 times for 2 minutes in the detecting part and then current flowing therein was measured over the concentration of the sample. The results are shown in FIG. 5.

Figure 5:
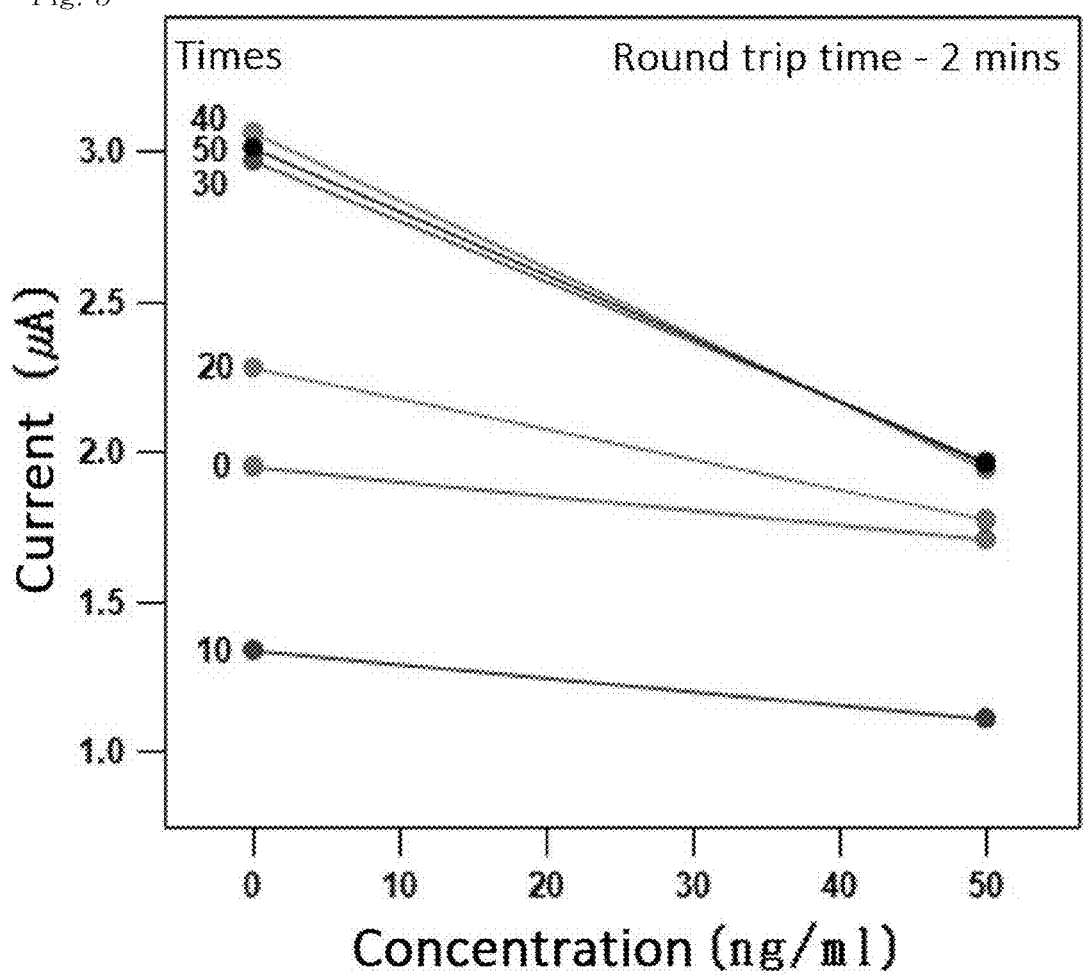
FIG. 5 is a graph illustrating the detection strength over the round-trips to the detecting part of the sample in the cartridge for sensor of the present invention.

FIG. 5 is a graph illustrating the detection strength over the numbers of round trip made by the sample in the detecting part measured using the cartridge for sensor of the present invention.

As shown in FIG. 5, considering the difference in signals and efficiency in signal detection, it was confirmed that 30 times of round trip for 2 minutes in the detecting part would be the most preferred condition for obtaining the highest detection strength.

INDUSTRIAL APPLICABILITY

As explained hereinbefore, the cartridge for sensor for detecting one or more components in a sample of the present invention not only enables quantitative/qualitative measurement of one or more components in a sample by one time sample injection but also facilitates mass-production with low cost owing to the simple structure and easiness in preparation and carry. Therefore, the cartridge of the present invention can be effectively used as the biosensor cartridge for field measurement.

The invention claimed is:

1. A cartridge for a sensor and for detecting one or more components in a sample comprising:
    a lower board, an upper board, an adhesive layer in between the two boards, and a microfluidic channel, wherein the microfluidic channel is formed in between the boards and the adhesive and connects an inlet (1), a sample chamber (2), a detecting part (3), and a disposal chamber (4) in that order wherein,
    the lower board comprises the inlet (1) through which a sample is injected;
    the sample chamber (2) to store the sample temporarily;
    the detecting part (3) to detect one or more components in the sample;
    the disposal chamber (4) to get rid of the sample;
    an air pump chamber (6) connected to the sample chamber (2) by an air channel (14) to transfer the sample temporarily stored in the sample chamber (2) to the disposal chamber (4) via the microfluidic channel (5);
    a reagent pump chamber (7) configured to house a pouch (13) to keep a reagent therein and transfer the reagent to the disposal chamber (4) via the detecting part (3), wherein the reagent pump chamber (7) comprises a pouch crushing pin, wherein the reagent pump chamber (7) is connected by the reagent channel (15) to the microfluidic channel (5) between the sample chamber (2) and the detecting part (3), and the upper board comprises a vent hole (8) which lies above the disposal chamber (4);

pores (9) which lie above the air pump chamber (6) and the reagent pump chamber (7); and a reading part (10) connected to a reading apparatus to detect a signal from the cartridge and stationed above the detecting part (3), wherein the lower board further comprises rubber stoppers (11) to seal the air pump chamber (6) and the reagent pump chamber (7) respectively, thereby functioning as an air pump and a reagent pump respectively, wherein the adhesive layer comprises pores just below and corresponding to the pores (9) of the upper board, the pores of the adhesive layer and the upper board reserving room for the rubber stopper (11).

2. The cartridge according to claim 1, wherein when the signal is an electrochemical signal, the detecting part in the lower board comprises an electrode part (16) composed of one or more standard electrodes and one or more working electrodes; an antibody or a molecular recognition material is fixed in each working electrode of the electrode part (16) to be reacted with different target components via immune response; and one or more label linked conjugates reacting to each target component in a sample are spread in one or more regions selected from the group consisting of the inlet (1), the sample chamber (2), and the microfluidic channel (5) between the inlet (1) and the detecting part (3).

3. The cartridge according to claim 1, wherein when the signal is an optical signal, an antibody or a molecular recognition material capable of reacting with different target components via immune response is fixed directly on the detecting part (3) or a detecting plate (11) fixed with the said antibody or the molecular recognition material is introduced in the detecting part (3); and one or more label linked conjugates reacting to each target component in a sample are spread in one or more regions selected from the group consisting of the inlet (1), the sample chamber (2), and the microfluidic channel (5) between the inlet (1) and the detecting part (3).

4. The cartridge according to claim 2, wherein the label linked conjugate is a monoclonal antibody conjugate or a polyclonal antibody conjugate prepared by combining an enzyme selected from the group consisting of peroxidase, alkaline phosphatase, acid phosphatase, tyrosinase, and glucose oxidase specifically with a detection target antigen, and the said label linked conjugate is characterized by selective binding to each target component in a sample.

5. The cartridge according to claim 3, wherein the label linked conjugate is a monoclonal antibody conjugate or a polyclonal antibody conjugate prepared by combining a fluorescein, colloidal gold, or colored latex bead specifically with a detection target antigen, and the said label linked conjugate is characterized by selective binding to each target component in the sample.

6. The cartridge according to claim 1, wherein when the signal is an electrochemical signal, the reading apparatus installed in the reading part (10) measures electrochemical signals.

7. The cartridge according to claim 1, wherein when the signal is an optical signal, the reading apparatus installed in the reading part (3) measures optical signals.

8. The cartridge according to claim 1, wherein the lower board includes the inlet cover (12) having a protrusion for tight sealing.

9. The cartridge according to claim 1, wherein the rubber stoppers (11) have wings (17) to seal respectively the air pump chamber (6) and the reagent pump chamber (7) tightly.

10. The cartridge according to claim 1, further comprising a pouch (13) to hold the reagents therein, which is included in the reagent pump chamber (7) to provide the reagent when the pouch is broken by the crushing pin during pumping of the reagent pump.

11. The cartridge according to claim 10, wherein when the signal is an electrochemical signal, the reagent comprises one or more substrates selected from the group consisting of naphthol AS, naphthol AS—BI, naphthol AS-D, naphthol AS-MX, p-aminophenylphosphate, hydrogen peroxide, and glucose, wherein when the signal is an optical signal, the reagent comprises a washing buffer.

12. The cartridge according to claim 1, further comprising a hotplate entry for introducing a hotplate into the cartridge to regulate reaction temperature below the detecting part (3).

13. The cartridge according to claim 1, wherein one or more vent holes are additionally equipped on the side of the lower board where the detecting part (3) is located in order to increase heat transfer efficiency.

14. The cartridge according to claim 1, wherein when the signal is an electrochemical signal, the lower board additionally comprises a fluidity sensing electrode to guide the reagent injection point by sensing the arrival of a sample between the detecting part (3) and the disposal chamber (4).

15. The cartridge according to claim 1, wherein when the signal is an electrochemical signal, the electrode part (16) additionally comprises one or more calibration electrodes to minimize the deviation of detection signals.

16. The cartridge according to claim 15, wherein the electrode part comprises a first calibration electrode to detect background signals and a second calibration electrode to detect saturating signals generated from the saturated label linked conjugate.

17. The cartridge according to claim 1, wherein the microfluidic channel is formed between the lower board and the adhesive layer; and the upper board and the adhesive layer, and the adhesive layer further comprises pores connected to the microfluidic channel (5).

18. The cartridge according to claim 1, wherein the air channel is positioned higher than the level of the sample stored temporarily in the sample chamber in order to prevent the flow of the sample into the air channel.

19. The cartridge according to claim 1, wherein the reagent channel is designed to prevent the flow of a sample into the reagent channel by forcing the reagent to flow the same direction as the flow of the sample in the microfluidic channel.

20. The cartridge according to claim 1, wherein the sample is blood, tears, sweat, saliva, or urine of mammals, or any solution generated from food.

* * * * *